United States Patent
Rogers et al.

(10) Patent No.: US 6,313,115 B1
(45) Date of Patent: Nov. 6, 2001

(54) BENZOFURAZAN COMPOUNDS WHICH ENHANCE AMPA RECEPTOR ACTIVITY

(75) Inventors: Gary A. Rogers, Santa Barbara; Christopher M. Marrs, Foothill Ranch, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/355,139

(22) PCT Filed: Feb. 13, 1998

(86) PCT No.: PCT/US98/02713

§ 371 Date: Oct. 4, 1999

§ 102(e) Date: Oct. 4, 1999

(87) PCT Pub. No.: WO98/35950

PCT Pub. Date: Aug. 20, 1998

Related U.S. Application Data

(63) Continuation-in-part of application No. 08/800,108, filed on Feb. 13, 1997, now Pat. No. 6,110,935.

(51) Int. Cl.⁷ .................. A61K 31/535; C07D 295/00
(52) U.S. Cl. .................... 514/231.2; 514/231.2; 514/231.5; 544/106
(58) Field of Search .......... 544/106; 514/231.2, 514/231.5

(56) References Cited

U.S. PATENT DOCUMENTS

| | | | |
|---|---|---|---|
| 3,981,864 | 9/1976 | Tanka et al. | 260/239 BC |
| 4,420,485 | 12/1983 | Davis et al. | 514/278 |
| 4,476,135 | 10/1984 | Neumann et al. | 424/270 |
| 5,032,604 | 7/1991 | Baldwin et al. | 514/361 |
| 5,112,824 | 5/1992 | Baldwin et al. | 514/253 |

FOREIGN PATENT DOCUMENTS

| | | |
|---|---|---|
| 0 431 943 A2 | 6/1991 | (EP) . |
| 0709384A | 5/1996 | (EP) . |
| WO 94/02475 | 2/1994 | (WO) . |
| 9402475 * | 2/1994 | (WO) . |
| WO 97/36907A | 10/1997 | (WO) . |

OTHER PUBLICATIONS

Bauer et al., (J.Med.Chem.Chem. 1976, vol. 19, No. 11, pp. 1315–1324).
Parham et al., (J. Org. Chem., 1976, vol. 41, No. 15, pp. 2629–2633).
(Neuroscience. 1997, pp. 465 and 480) Edited by Dale Purves.

* cited by examiner

*Primary Examiner*—Sakiha N. Qazi
(74) *Attorney, Agent, or Firm*—Henry D. Coleman; R. Neil Sudol; William J. Sapone

(57) ABSTRACT

Compounds of general structural formula (I) are shown to have AMPA receptor enhancing properties. The compounds are useful for such therapeutic purposes as facilitating the learning of behaviors dependent upon AMPA receptors, and in treating conditions, such as memory impairment, in which AMPA receptors, or synapses utilizing these receptors, are reduced in numbers or efficiency. They may also be used to enhance excitatory synaptic activity in order to restore an imbalance between brain subregions, as in treatment of schizophrenia or schizophreniform behavior.

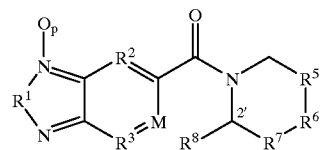

21 Claims, 3 Drawing Sheets

BENZOFURAZAN COMPOUNDS WHICH ENHANCE AMPA RECEPTOR ACTIVITY

RELATED APPLICATION

This application is a §371 of international application no. PCT/US98/02713, which is a continuation-in-part application of U.S. application Ser. No. 08/800,108, filed Feb. 13, 1997, now U.S. Pat. No. 6,110,935.

FIELD OF THE INVENTION

This invention relates to the prevention and treatment of cerebral insufficiency, including enhancement of receptor functioning in synapses in brain networks responsible for higher order behaviors. These brain networks are involved in cognitive abilities related to memory impairment, such as is observed in a variety of dementias, and in imbalances in neuronal activity between different brain regions, as is suggested in disorders such as schizophrenia. In a particular aspect, the invention relates to compounds useful for treatment of such conditions, and methods of using these compounds for such treatment.

BACKGROUND OF THE INVENTION

The release of glutamate at synapses at many sites in mammalian forebrain stimulates two classes of postsynaptic receptors. These classes are usually referred to as AMPA/quisqualate and N-methyl-D-aspartic acid (NMDA) receptors. AMPA/quisqualate receptors mediate a voltage independent fast excitatory post-symptic current (the fast EPSC), whereas NMDA receptors generate a voltage-dependent, slow excitatory current. Studies carried out in slices of hippocampus or cortex indicate that the AMPA receptor mediated fast EPSC is generally the dominant component by far at most glutamatergic synapses.

AMPA receptors are not evenly distributed across the brain but rather are largely restricted to telencephalon and cerebellum. These receptors are found in high concentrations in the superficial layers of neocortex, in each of the major synaptic zones of hippocampus, and in the striatal complex, as reported by Monaghan et al. in *Brain Research* 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For these reasons, drugs that enhance the functioning of AMPA receptors could have significant benefits for intellectual performance. Such drugs should also facilitate memory encoding. Experimental studies, such as those reported by Arai and Lynch, *Brain Research* 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA form of glutamate receptors facilitate the induction of LTP and the acquisition of learned tasks, as measured by a number of paradigms. See, for example, Granger et al., *Synapse* 15:326–329 (1993); Staubli et al., PNAS 91:777–781 (1994); Arai et al., Brain Res. 638:343–346 (1994); Staubli et al., PNAS 91:11158–11162 (1994); Shors et al., *Neurosci. Let.* 186:153–156 (1995); Larson et al., J. Neurosci. 15:8023–8030 (1995); Granger et al., *Synapse* 22:332–337 (1996); Arai et al., JPET 278:627–638 (1996); Lynch et al., *Internat. Clin. Psychopharm.* 11:13–19 (1996); and Lynch and Rogers, PCT Pubn. No. WO 94/02475. There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, *Neuroscience* 49:1–6 (1992).

A possible prototype for a compound that selectively facilitates the AMPA receptor has been described by Ito et al., *J. Physiol.* 424:533–543 (1990). These authors found that the nootropic drug aniracetam (N-anisoyl-2-pyrrolidinone) increases currents mediated by brain AMPA receptors expressed in Xenopus oocytes without affecting responses by gamma-aminobutyric acid (G ABA), kainic acid (KA), or NMDA receptors. Infusion of aniracetam into slices of hippocampus was also shown to increase the size of fast synaptic potentials without altering resting membrane properties. It has since been confirmed that aniracetam enhances synaptic responses at several sites in hippocampus, and that it has no effecton NMDA-receptor mediated potentials. See, for example, Staubli et al., *Psychobiology* 18:377–381 (1990) and Xiao et al., *Hippocampus* 1:373–380 (1991).

Aniracetam has been found to have a rapid onset and washout, and can be applied repeatedly with no apparent lasting effects, which are desirable features for behaviorally relevant drugs. Aniracetam does present several disadvantages, however. The peripheral administration of aniracetam is not likely to influence brain receptors. The drug works only at high concentrations (approx. 1.0 mM), and about 80% of the drug is converted to anisoyl-GABA following peripheral administration in humans (Guenzi and Zanetti, *J. Chromatogr.* 530:397–406 (1990)). The metabolite, anisoyl-GABA, has been found to have less activity than aniracetam.

A class of AMPA receptorenhancing compounds that does not display the low potency and inherent instability characteristics of aniracetam has been described (Lynch and Rogers, PCT Pubn. No. WO 94/02475). These compounds, termed "AMPAKINES"™, are substituted benzamides which include, for example, 1-(1,3-5 benzodioxol-5-ylcarbonyl)piperidine. They are chemically more stable than aniracetam and show improved bioavailability as judged by experiments performed by Positron Emission Tomography (PET) (see, for example, Staubli et al., in *PNAS* 91:11158–11162 (1994).

Another class of Ampakines, benzoxazines, has been discovered recently to have very high activity in in vitro and in vivo models for assessing the probability of producing cognition enhancement, as described in PCT Pubn. No. WO 97/36907, "Benzoxazines for Enhancing Synaptic Response", by Rogers and Lynch. Some, but not all, of these compounds show activity in a rat model for the human disease, schizophrenia (Larson et al., *Brain Res.* 728: 353–356 (1996)).

Certain substituted benzofurazan and benzothiadiazole compounds have been found to be significantly and surprisingly more potent in the animal model of schizophrenia than these previously reported compounds, and are also effective in cognition enhancement. These compounds are disclosed herein.

SUMMARY OF THE INVENTION

The present invention includes, in one aspect, compounds as shown and described in Section II of the Detailed Description, following. The compounds are effective to increase AMPA receptor-mediated responses and are thus useful for a variety of purposes. These include facilitating the learning of behaviors dependent upon AMPA receptors, treating conditions in which AMPA receptors, or synapses utilizing these receptors, are reduced in numbers or efficiency, and enhancing excitatory synaptic activity in order to restore an imbalance between brain subregions. The invention thereby provides a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior.

According to the method, the subject is treated with an effective amount of a compound as shown and described in Section II of the Detailed Description, following, in a pharmaceutically acceptable carrier. As demonstrated below, the compounds are significantly more potent than previously described compounds in increasing AMPA receptor function in slices of rat hippocampus, in animal models of schizophrenia and depression, and in enhancing cognitive performance, such as performance in an 8-arm radial maze.

These and other objects and features of the invention will become more fully apparent when the following detailed description of the invention is read in conjunction with the accompanying drawings.

DETAILED DESCRIPTION OF THE INVENTION

I. Definitions

Figure 1:
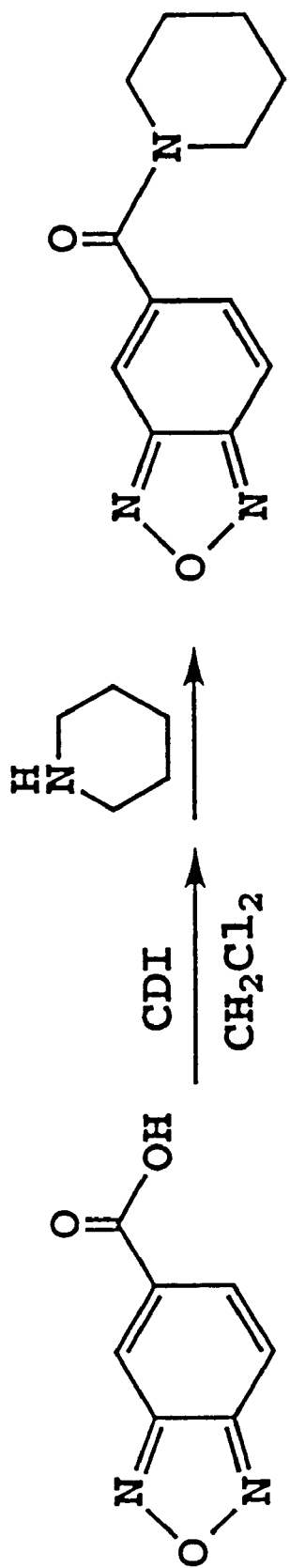
FIG. 1 shows a method of preparing a preferred compound of the invention.

The terms below have the following meanings unless indicated otherwise.

"Alkyl" refers to a fully saturated monovalent radical containing carbon and hydrogen, and which may be cyclic, branched or a straight chain. Examples of alkyl groups are methyl, ethyl, n-butyl, n-heptyl, isopropyl, 2-methylpropyl, cyclopropyl, cyclo-propylmethyl, cyclobutyl, cyclopentyl, cyclopentylethyl, and cyclohexyl.

"Aryl" refers to a substituted or unsubstituted monovalent aromatic radical having a single ring (e.g., benzene) or multiple condensed rings (e.g., naphthyl). Other examples include heterocyclic aromatic ring systems having one or more nitrogen, oxygen, or sulfur atoms in the ring, such as imidazole, furyl, pyrrole, pyridyl, and indole.

The term "effective amount" refers to the amount of a selected compound of formula I which is necessary to enhance glutamatergic synaptic response by increasing AMPA receptor activity. The precise amount required will vary depending upon the particular compound selected, the age and weight of the subject, route of administration, and so forth, but may be easily determined by routine experimentation.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

II. AMPA Receptor Enhancing Compounds

The present invention is directed, in one aspect, to compounds having AMPA receptor enhancing properties. These are compounds having the structure I, below:

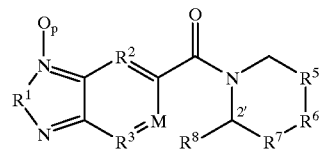

in which:

$R^1$ is oxygen or sulfur;

$R^2$ and $R^3$ are independently selected from the group consisting of —N=, —CR=, and —CX=;

M is =N— or =$CR^4$—, wherein $R^4$ and $R^8$ are independently R or together form a single linking moiety linking M to the ring vertex 2', the linking moiety being selected from the group consisting of a single bond, —CRR'—, —CR=CR'—, —C(O)—, —O—, —S(O)$_y$—, —NR—, and —N=; and $R^5$ and $R^7$ are independently selected from the group consisting of —(CRR')$_n$—, —C(O)—, —CR=CR'—, —CR=CX—, —CRX—, —CXX'—, —S—, and —O—, and $R^6$ is selected from the group consisting of —(CRR')$_m$—, —C(O)—, —CR=CR'—, —CRX—, —CXX'—, —S—, and —O—;

wherein

X and X' are independently selected from —Br, —Cl, —F, —CN, —NO$_2$, —OR, —SR, —NRR', —C(O)R, —CO$_2$R, or —CONRR', where two R or R' groups on individual or separate X groups may together form a ring;

R and R' are independently selected from (i) hydrogen, (ii) $C_1$–$C_6$ branched or unbranched alkyl, which may be unsubstituted or substituted with one or more functionalities selected from halogen, nitro, alkoxy, hydroxy, alkylthio, amino, keto, aldehyde, carboxylic acid, carboxylic ester, or carboxylic amide, and where two such alkyl groups on a single carbon or on adjacent carbons may together form a ring, and (iii) aryl, which may be unsubstituted or substituted with one or more functionalities selected from halogen, nitro, alkoxy, hydroxy, aryloxy, alkylthio, amino, keto, aldehyde, carboxylic acid, carboxylic ester, or carboxylic amide;

m and p are, independently, 0 or 1; and n and y are, independently, 0, 1 or 2.

Preferred subsets of the compounds encompassed by formula I include those in which p is 0, those in which $R^2$ and $R^3$ are —CR= and M is =$CR^4$, particularly where $R^4$ its hydrogen, and those in which $R^1$ is oxygen. A particularly preferred subset is one in which all of the above qualifications apply, and more preferably in which $R^5$ and $R^7$ are —(CRR')$_n$— and $R^6$ is (CRR')$_m$—; that is, certain 5-carboxamido benzofurazan derivatives containing different-sized saturated heterocyclic rings linked to the carbonyl group.

Preferred compounds of this subset are those in which R and R' are selected from (i) hydrogen or (ii) alkyl, as defined above. A particularly preferred compound of this group is 1-(benzofurazan-5-ylcarbonyl)piperidine, designated herein as compound 2. Also preferred is the corresponding compound in which R' is sulfur; that is, 1-(benzo-2,1,3- thiadiazole-5-ylcarbonyl)piperidine, designated herein as compound 1. Other examples, having differently sized rings (where n is 1 and m is 0 or 2, respectively) include 1-(benzofurazan-5-ylcarbonyl)pyrrolidine (11) and 1-(benzofurazan-5-ylcarbonyl)hexamethyleneimine (14).

A second preferred subset of the compounds of formula I is that in which p is 0, $R^4$ and $R^8$ are both hydrogen, $R^6$ is —(CRR')$_m$', $R^7$ is —(CRR')$_n$—, and $R^5$ is —CR=CX— or —CR=CR'—, that is, the heterocyclic ring includes a double bond. A further preferred class of this second subset is that in which m is 0. Particularly preferred examples of this class are those compounds in which $R^1$ is oxygen, n is 1, and R and R' are hydrogen, that is, 1-(benzofurazan-5-ylcarbonyl)-1,2,3,6-tetrahydropyridine, designated herein as compound 3, and 1-(benzofurazan-5-ylcarbonyl)-1,2,3,6-tetrahydro4-fluoropyridine, designated herein as compound 6. A further example, having a 5-membered ring (m and n are both zero), is 1-(benzofurazan-5-ylcarbonyl)-pyrroline (12).

A third preferred subset of formula I includes those compounds in which p is 0, $R^1$ is oxygen, $R^4$ and $R^8$ are both hydrogen, $R^5$ and $R^7$ are —(CRR')$_n$—, and $R^6$ is —C(O)—, —CRX—, CXX'—, —O—, or —S—. A further preferred class of this third subset is that in which $R^6$ is —CRX—or —CXX'—, where R and X are each selected from the groups defined above, and n is 1. Two particularly preferred examples of this class are 1-(benzofurazan-5-ylcarbonyl)4'-cyanopiperidine (compound 8) and 1-(benzofurazan-5-ylcarbonyl)-4'-hydroxypiperidine (compound 9). Also preferred are those in which X is fluorine and R and R' are hydrogen; that is, 1-(benzofurazan-5-ylcarbonyl)4'-fluoropiperidine and 1-(benzofurazan-5-ylcarbonyl)-4',4'-difluoropiperidine, designated herein as compounds 4 and 5, respectively. Other examples include the corresponding 4-methylpiperidine and 4-methoxypiperidine derivatives (13 and 17, respectively).

When any of $R^5$, $R^6$, and $R^7$ is CXX', two groups X and X' on the same or adjacent carbons may form a ring, as noted above. An example is 1-(benzofurazan-5-ylcarbonyl)-1,4-dioxa-8-azaspiro[4,5]decane (15).

Another preferred class of this third subset is that in which n is 1, R and R' are hydrogen, and $R^6$ is oxygen or sulfur. This class includes morpholino and thiomorpholino amides of benzofurazan, i.e. N-(benzofurazan-5-ylcarbonyl) morpholine (7) and N-(benzofurazan-5-ylcarbonyl) thiomorpholine (10). In compound 16, derived from 4pyridinone, R' is C(O)—.

A fourth preferred subset of the compounds of formula I is that in which M is =CRW—, where $R^4$ and $R^8$ together form a single linking moiety linking M to the ring vertex 2'. This linking moiety is selected from the group consisting of a single bond, —CRR'—, —CR=CR'—, —C(O)-, —O—, —S—, —NR—, and —N=. Preferred compounds of this fourth subset include those in which p is 0, those in which $R^1$ is oxygen, and those in which $R^2$ and $R^3$ are —CR=, where R is defined as above. Particularly preferred compounds are those in which all of the above qualifications apply; that is, certain tetracyclic benzofurazan amides, such as those represented in FIG. 2. A preferred group of these compounds includes those in which the linking moiety is selected from —CRR'—, —O—, —S—, and —N=. Preferably, $R^5$ and $R^7$ are —(CRR')$_n$—, and $R^6$ is —(CRR')$_m$. More preferably, in this case, n is 1, and m is 0 or 1, giving a 5-membered or 6-membered heterocyclic ring, respectively, as the rightmost fused ring. Of the preferred linking moieties, —CRR'—, oxygen, sulfur, and —N=, oxygen and imino (—N=) are particularly preferred, with oxygen being most preferred.

III. Preparation of Subject Compounds

The compounds of the present invention can be synthesized in a variety of ways, using conventional synthetic chemistry techniques. Methods for the preparation of the compounds of the present invention include the following.

Compounds of the invention in which $R^4$ and $R^8$ do not form a linking moiety are conveniently prepared, as shown in FIG. 1, by activation of the carboxyl group of an appropriately substituted benzoic acid, or, alternatively, a nicotinic, pyrazinoic, pyridizine carboxylic, or pyrimidine carboxylic acid, with carbonyldiimidazole or another activating group, e.g. thionyl chloride, in an anhydrous solvent such as dichloromethane, chloroform, tetrahydrofuran, or ethyl acetate. A cyclic amine is then reacted with the activated carboxyl group. The cyclic amine preferably includes, in accordance with the preferred structures described above, an optionally substituted piperidine derivative. The ring may also include unsaturation or an oxygen or sulfur ring atom, and larger or smaller ring sizes are also contemplated. A large selection of such amines is commercially available; alternatively, they may be prepared using well established synthetic methods.

Examples 1–20 describe preparation of representative compounds of the invention, designated herein as compounds 1 to 18, according to the methods described above.

Compounds of the invention in which $R^4$ and $R^8$ form a linking moiety may be prepared according to methods such as those shown in FIGS. 2A–2D. Although the illustrated preparations employ a benzofurazan nucleus, similar methods may be used to prepare other compounds of the invention, e.g. the corresponding benzothiadiazoles and other nitrogen-containing heteroaromatic systems.

Figures 2A, 2B:
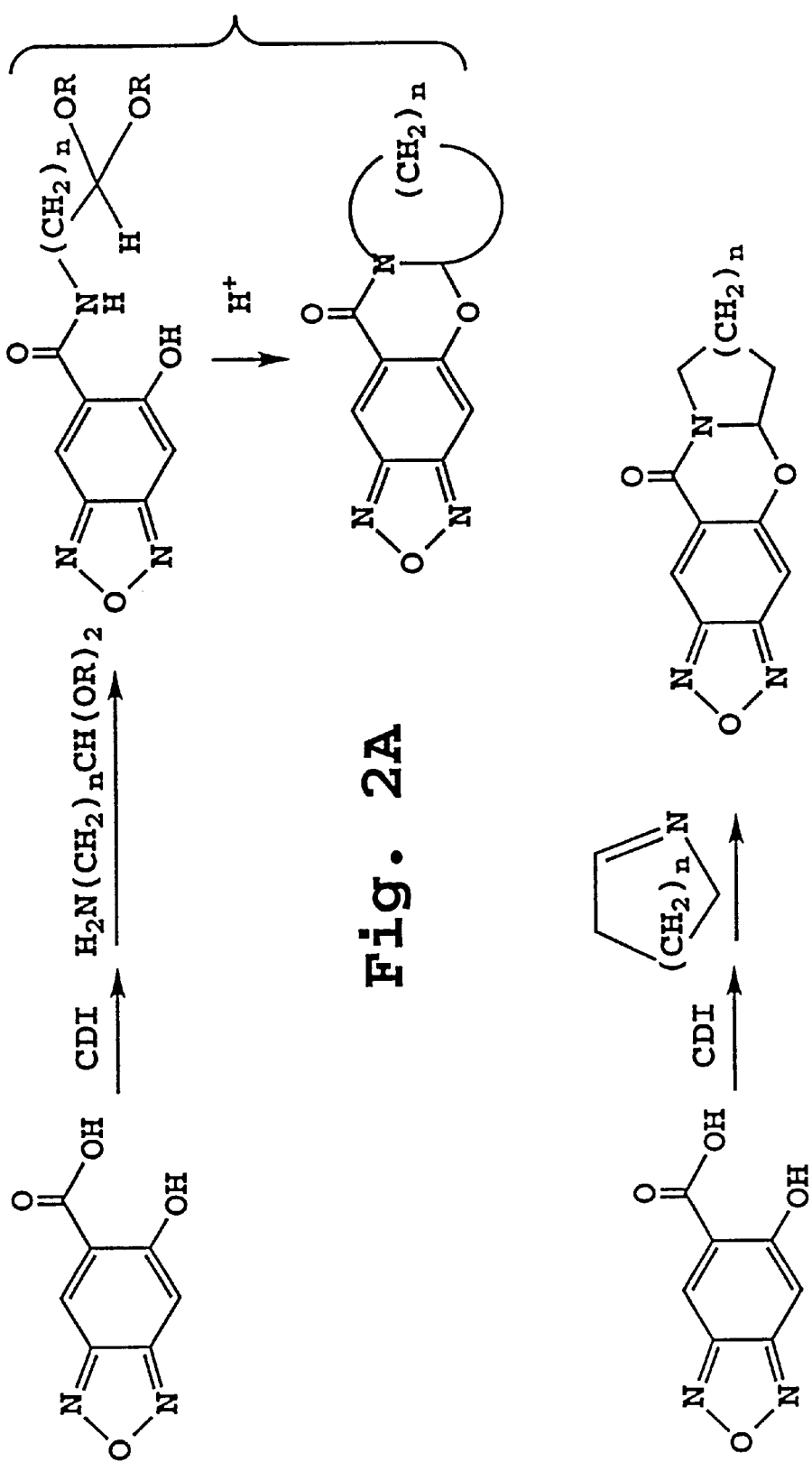
FIGS. 2A–2D show methods of preparing tetracyclic compounds that form one embodiment of the invention.

As shown in FIG. 2A, activation of the carboxyl group of an appropriately substituted salicylic acid with carbonyldiimidazole, in an anhydrous solvent such as dichloromethane, chloroform, tetrahydrofuran, ethyl acetate, or the like, is followed by addition of a suitable aminoalkylacetal. The resulting amide acetal is treated with a strong acid, such as an alkyl or aryl sulfonic acid, or trifluoroacetic acid in a solvent of low basicity, such as dichloromethane, to effect cleavage of the acetal and cyclization to a tetracyclic substituted benzoxazine, as shown, in which the linking moiety formed by $R^4$ and R' is oxygen. An alternative method of preparation, shown in FIG. 2B, reacts the activated salicylate with a cyclic imine, such as 1-pyrroline or 2,3,4,5-tetrahydropyridine.

Figure 2C:
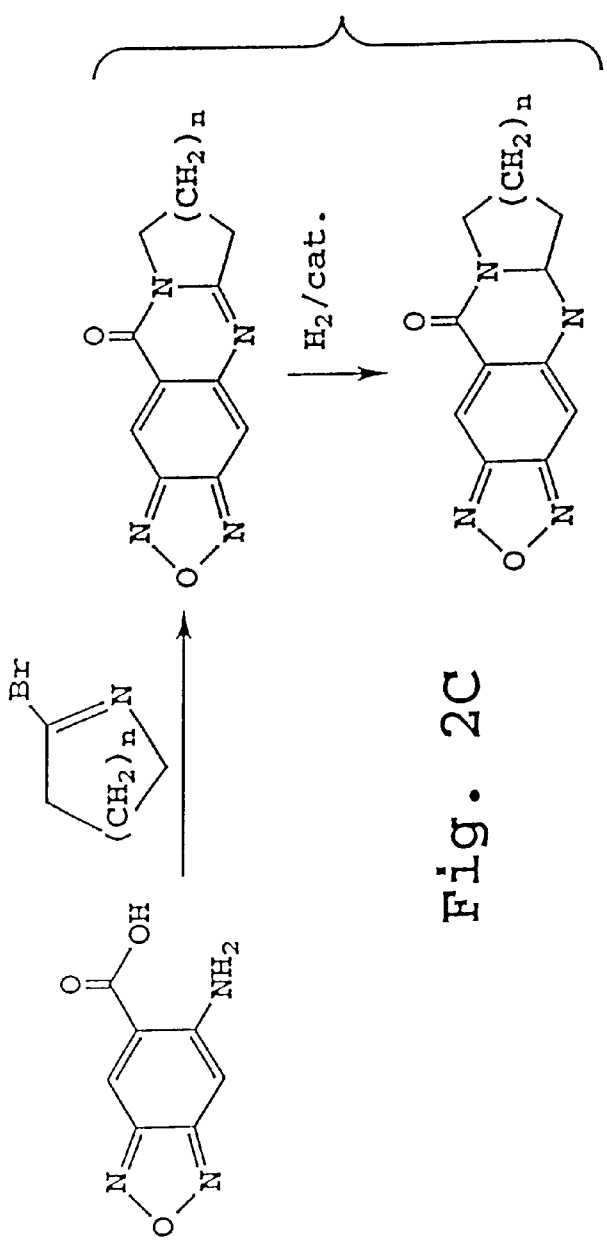

FIG. 2C shows the reaction of a suitably substituted anthranilate ester with a cyclic haloimine, such as a 2-chloro- or 2-bromoimidate, to yield a tetracyclic compound in which the linking moiety formed by $R^4$ and $R^8$ is an imino group. This group may be subsequently reduced by, for example, catalytic hydrogenation, to give an amino linking moiety.

Figure 2D:
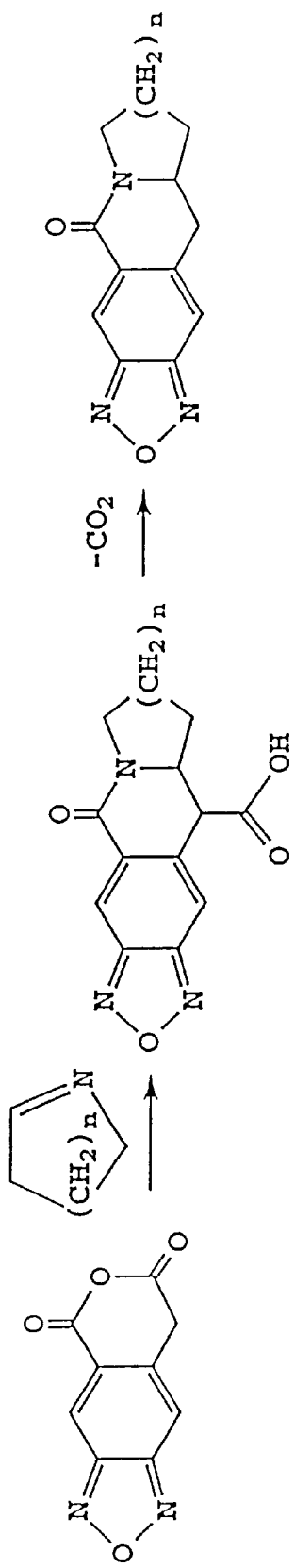

FIG. 2D shows the reaction of a suitably substituted homophthalic anhydride with a cyclic imine, such as 1-pyrroline or 2,3,4,5-tetrahydropyridine, followed by decarboxylation, to yield a tetracyclic compound in which the linking moiety formed by $R^4$ and R' is a —CH$_2$—or —CRR'— group. (See, for example, Cushman et al., *J. Org. Chem.* 45:5067–5073 (1980), and Smith et al., *J. Heterocyclic Chem.* 28:1813–1815 (1991).)

IV. Method of Treatment

According to a further aspect of the invention, the subject compositions are useful for the treatment of schizophrenia or schizophreniform behavior in a mammalian subject, or for treating impairment in memory or other cognitive functions. Such maladies are symptomatic of a hypoglutamatergic condition, or of deficiencies in the number or strength of excitatory synapses, or in the number of AMPA receptors. Because treatment of a subject with the subject compositions enhances AMPA receptor activity, such treatment may also be used to facilitate the learning of behaviors dependent upon AMPA receptors. The method of treatment comprises administering to the subject, in a pharmaceutically acceptable carrier, an effective amount of a compound having the formula:

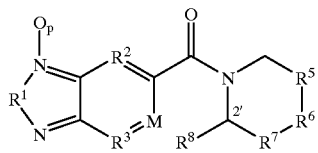

wherein
$R^1$ is oxygen or sulfur;
$R^2$ and $R^3$ are independently selected from the group consisting of —N=, —CR=, and —CX=;
M is =N— or =CR$^4$—, wherein $R^4$ and $R^8$ are independently R or together form a ingle linking moiety linking M to the ring vertex 2', the linking moiety being selected from the group consisting of a single bond, —CRR'—, —CR=CR'—, C(O)—, —O—, —S(O)$_y$—, —NR—, and —N=;
$R^5$ and $R^7$ are independently selected from the group consisting of —(CRR')$_n$—, —C(O)—, —CR=CR'—, —CR=CX—, —CRX—, —CXX'—, —S—, and —O—, and $R^6$ is selected from the group consisting of —(CRR')$_m$—, —C(O)—, —CR=CR'—, —CRX—, —CXX'—, —S—, and —O—;
wherein
X and X' are independently selected from —Br, —Cl, —F, —CN, —NO$_2$, —OR, —SR, —NRR', —C(O)R, —CO$_2$R, or —CONRR', wherein two groups R or R' on an individual group X, or on two adjacent groups X, may together form a ring; and and
R and R' are independently selected from (i) hydrogen, (ii) $C_1$–$C_6$ branched or unbranched alkyl, which may be unsubstituted or substituted with one or more functionalities selected from halogen, nitro, alkoxy, hydroxy, alkylthio, amino, keto, aldehyde, carboxylic acid, carboxylic ester, or carboxylic amide, and wherein two such alkyl groups on a single carbon or on adjacent carbons may together form a ring, and (iii) aryl, which may be unsubstituted or substituted with one or more functionalities selected from halogen, nitro, alkoxy, hydroxy, aryloxy, alkylthio, amino, keto, aldehyde, carboxylic acid, carboxylic ester, or carboxylic amide;
m and p are, independently, 0 or 1; and
n and y are, independently, 0, 1 or 2.

Of the compounds administered according to the method, preferred groups include those described in Section II, above. Particularly preferred are those compounds designated as compounds 1 through 9, with compounds 2, 7, 8 and 9 being most preferred The compounds administered in accordance with the method have been found to be more effective than previously described compounds in enhancing AMPA receptor activity, as shown in the in vitro and in vivo tests described below.

V. Biological Activity
A. Enhancement of AMPA Receptor Function

Synaptic responses mediated by AMPA receptors are increased according to the method of the invention, using the compounds described herein. These compounds are demonstrated, in the Examples that follow, to be substantially more potent than previously-described compounds in increasing AMPA receptor function in slices of rat hippocampus. This in vitro assay is described as follows, and in Example 21, below.

The field EPSP (excitory post-synaptic potential) recorded in field CAI after stimulation of CA3 axons is known to be mediated by AMPA receptors, which are present in the synapses (Kessler et al., *Brain Res.* 560: 337–341 (1991)). Drugs that selectively block the receptor selectively block the field EPSP (Muller et al., *Science*, supra). Aniracetam, which has been shown to increase the mean open time of the AMPA receptor channel, increases the amplitude of the synaptic current and prolongs its duration (Tang et al., *Science*, supra). These effects are mirrored in the field EPSP (see, for example, Staubli et al., *Psychobiology*, supra; Xiao et al., *Hippocampus*, supra; Staubli et al., *Hippocampus* 2: 4958 (1992)). Similar results have been reported for the previously disclosed stable benzamide analogs of aniracetam (Lynch and Rogers, PCT Pubn. No. WO 94/02475).

To obtain the data shown in Table I, a bipolar nichrome stimulating electrode was positioned in the dendritic layer (stratum radiatum) of the hippocampal subfield CA1 close to the border of subfield CA3, as described in Example 21. Current pulses (0.1 msec) through the stimulating electrode activate a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the post-synaptic cell. This current results in a voltage in the extracellular space (the field EPSP), which is recorded by a high impedance recording electrode positioned in the middle of the stratum radiatum of CA1.

The intensity of the stimulation current was adjusted to produce half-maximal EPSPs (typically about 1.5–2.0 mV). Paired stimulation pulses were given every 40 sec with an interpulse interval of 200 msec, as described further in Example 21.

Hippocampal slices were maintained in a recording chamber continuously perfused with artificial cerebrospinal fluid (ACSF). During 15–30 minute intervals, the perfusion medium was switched to one containing various concentrations of the test compounds. Responses collected immediately before and at the end of drug perfusion were superimposed in order to calculate the percent increase in EPSP amplitude.

Figure 3:
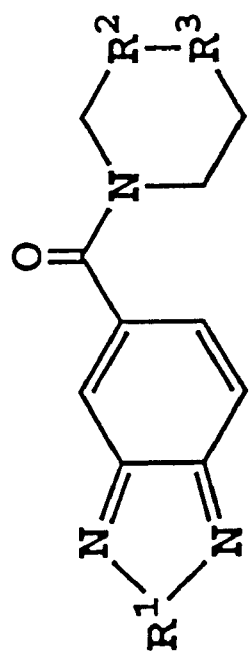
FIG. 3 represents a selection of compounds useful in practicing the method of the invention.

Invention compounds 1–9, as shown in FIG. 3 and Table 1 below, and reference compound CS516 (1-(quinoxalin-6-ylcarbonyl)piperidine), disclosed in PCT Pubn. No. WO 94/02475, were assayed in the physiological test system described above. The first data column of Table 1 shows the estimate of the concentration of each test compound that would be required to increase the amplitude of the field EPSP to a value 10% above the baseline level.

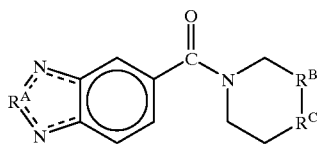

TABLE I

| Compound # | $R^A$ | $R^B$ | $R^C$ | Amp[1] (μM) | $MED_s$[2] (mg/kg) | $MED_c$[3] (mg/kg) | $MED_D$[4] (mg/kg) |
|---|---|---|---|---|---|---|---|
| CX516 | CHCH | $CH_2$ | $CH_2$ | 50 | 10 | 15 | 5 |
| 1 | S | $CH_2$ | $CH_2$ | <100 | NT | NT | NT |
| 2 | O | $CH_2$ | $CH_2$ | 3 | 0.1 | 0.1 | 0.01 |
| 3 | O | CH | CH | 100 | NT | NT | NT |
| 4 | O | $CH_2$ | CHF | 30 | 1 | NT | NT |
| 5 | O | $CH_2$ | $CF_2$ | 50 | 1 | NT | NT |
| 6 | O | $CH_2$ | CF | 30 | NT | NT | NT |
| 7 | O | $CH_2$ | O | 3 | ND | 0.1 | NT |
| 8 | O | $CH_2$ | CHCN | 1 | ND | 0.1 | NT |
| 9 | O | $CH_2$ | CHOH | 20 | ND | 0.1 | 0.01 |

[1]Concentration of compound that causes a 10% increase in the amplitude of the field EPSP in Field CA1 of rat hippocampal slice.
[2]Minimum Effective Dose that produces a statistically significant improvement in behavior in the animal model of schizophrenia.
[3]Minimum Effective Dose that produces a statistically significant improvement in behavior in the eight-arm radial maze task for cognition/memory enhancement.
[4]Minimum Effective Dose that produces a statistically significant improvement in behavior in an animal model of depression.
NT = Not tested;
ND = Not determined As the data in Table 1 show, the present compounds produced a dose-dependent increase in the amplitude of the EPSP and were effective at concentrations as low as 3 uM. The majority of the tested compounds were equally or more effective, up to a factor of about fifty, than the reference compound, CX516, in increasing AMPA receptor function. Compounds 2, 4, and 6–9 were particularly effective.

Studies that compared the effects of AMPA modulators on monosynaptic (as reported here) and polysynaptic responses demonstrated that a 10% increase in the amplitude of the monosynaptic field EPSP was amplified to an increase of 300% on a trisynaptic response (Servio et al., *Neuroscience* 74: 1025–1035 (1996)). Furthermore, the 10 concentration of the modulator that evoked these responses was shown to exist in plasma from behaviorally relevant doses (Granger et al., *Synapse*, supra). Thus, a 10% increase in amplitude of the monosynaptic field EPSP, as reported in the table, is likely to represent a behaviorally relevant plasma concentration.

B. Behavioral Testing

The compounds of the invention are also effective in relevant animal models of disease, such as schizophrenia and depression, and in models of cognitive performance, such as performance in an 8-arm radial maze.

The second data column in Table 1 shows the Minimum Effective Dose ($MED_s$) for efficacy in the methamphetamine/rat model, which has proven useful in assessing the efficacy of neuroleptic drugs for the treatment of schizophrenia (Larson et al., *Brain Res.*, supra). The dose recorded is that which reduced the hyperactivity and/or the stereotypic activity induced by acute administration of 2 mg/kg methamphetamine in rats, as described in Example 22.

All of the compounds tested were significantly more effective than the reference compound, as shown in the Table, in that a ten-fold or greater reduction in dose produced, an equivalent effect. Compound 2 was equally effective at a hundred-fold reduction in dose.

The third data column shows the MED for efficacy to improve performance in the eight-arm radial maze task, which tests for improved memory and cognition ($MED_c$). This task has been described previously (Staubli et al., *PNAS* 91:777–781 (1994)) and Lynch and Rogers, PCT Pubn. No. WO 94/02475). Again, all of the tested compounds (2 and 7–9) were several times more potent than CX516 in this test.

The fourth column in the Table shows the MED that produces a statistically significant improvement in behavior in an animal model of depression (MEDD), as described by Malatynska and Kostowski, *Pol. J. Pharmacol.* 40, 357–364 (1984). Compounds 2 and 9 were tested and, again, were much more potent (approximately 500 fold) than the reference compound.

VI. Administration. Dosages, and Formulation

As noted above, the compounds and method of the invention increase AMPA receptor-mediated responses, and are useful for the treatment of hypoglutamatergic conditions. They are also useful for treatment of conditions such as impairment of memory or other cognitive functions, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning of behaviors dependent upon AMPA receptors.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection. Subjects contemplated for treatment according to the method of the invention include humans, domesticated animals, laboratory animals, and the like.

Formulations containing the compounds of the invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols or the like, preferably in unit dosage forms suitable for simple administration of precise dosages.

The compositions typically include a conventional pharmaceutical carrier or excipient and may additionally include other medicinal agent, carriers, adjuvants, and the like. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20%), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see "Remington's Pharmaceutical Sciences" (17th Ed., Mack Pub. Co, 1985). The composition to be administered will contain a quantity of the selected compound in a pharmaceutically effective amount for effecting increased AMPA receptor currents in a subject.

EXAMPLES

The following examples illustrate but are not intended in any way to limit the invention.

Unless otherwise stated, all temperatures are given in degrees Celsius. All $^1$H NMR spectra were obtained in deuterochloroform as solvent using tetramethylsilane as an internal standard. Infrared (IR) spectra were recorded as thin films on a Fresnel crystal in a ATI Mattson Gemini series FTIR.

Note: The distillation of any of the following compounds should be conducted using extreme caution, The danger of release of gaseous decomposition products is exacerbated by increased scale of the reaction. An alternative purification method, using activated charcoal, is described in Example 2, Method B, below.

EXAMPLE 1

1-(Benzo-2,1,3-thiadiazole-5-ylcarbonyl)piperidine (1)

Trimethylaluminum (2M in toluene; 3.0 mL, 6.0 mmol) was diluted into 30 mL dichloromethane to which piperidine (0.55 g, 6.5 mmol) and methyl benzo-2,1,3-thiadiazole-5-carboxylate (1.16 g, 6.00 mmol) were added. The reaction was stirred at room temperature for 2 hours and concentrated to one-half the volume by rotary evaporation. Dry toluene (25 mL) was added and the reaction solution was heated to 80° C. for 1 hour. Additional piperidine (about 0.2 g) was added and the temperature was increased to 100° C. for 1 hour. The solution was allowed to cool to room temperature and stirred overnight, at which time it was quenched with 10% citric acid and hydrochloric acid. The solution was diluted with ethyl acetate and sequentially washed with 10% citric acid, saturated sodium hydrogen phosphate and saturated sodium chloride, and subsequently dried over anhydrous sodium sulfate. The solution was concentrated onto silica and product was eluted with hexane/ethyl acetate (3:1). Purification by distillation in a kugelrohr at 18° C. and 0.5 mmHg yielded 1-(benzo-2,1,3-thiadiazole-5-ylcarbonyl) piperidine, 1 (1.29 g, 87%) as a pale yellow oil. IR: 2920, 2855, 1633, 1478, 1439, 1280, 1223, 1001, 816, and 748 cm$^{-1}$. $^1$H NMR (500 MHz): δ 8.06 (1H, d, J=9.1 Hz); 8.02 (1H, s); 7.63 (1H, t, J=9.0 and 1.5 Hz); 3.77 (2H, br s); 3.40 (2H, br s); 1.72 (4H, br s); and 1.57 ppm (2H, br s).

EXAMPLE 2

1-(Benzofurazan-5-ylcarbonyl)piperidine (2)

Method A

Benzofurazan-5-carboxylic acid (2.0 g, 12.2 mmol) was suspended in 10 mL dichloromethane. Carbonyl diimidazole (2.0 g, 12.3 mmol) was added, which caused dissolution with gas evolution. The resulting yellow solution was stirred for 40 minutes at room temperature, following which, piperidine (1.2 g, 14.1 mmol) was added. The solution was stirred overnight and then concentrated onto silica. Product was eluted with hexane/ethyl acetate (2:1) and purified by distillation in a kugelrohr at 155–170° C. and 0.5 mmHg. 1-(Benzofurazan-5-ylcarbonyl)piperidine, 2 (2.78 g, 99%), initially a pale yellow oil, crystallized upon cooling. M.p. 88.5–90.5° C. IR: 2938, 2857, 1630, 1519, 1439, 1266, 1223, 996, 881, 816, and 740 cm$^{-1}$. $^1$H NMR (500 MHz): δ 7.90 (1H, d, J=9.7 Hz); 7.84 (1H, s); 7.44 (1H, dd, J=9.4 and 1.4 Hz); 3.74 (2H, br s); 3.39 (2H, br s); 1.72 (4H, br s); and 1.57 ppm (2H, br s).

Method B

A 5-L flask was charged with ethyl acetate (2.3 L) and carbonyl diimidazole (500.0 g, 2.48 mol) to which 4-chloro-3-nitrobenzoic acid (402.5 g, 2.48 mol) was added in portions over 1 hour. The solution was stirred for an additional 1.5 hours. Piperidine (222.2 g, 2.60 mol) was added dropwise over 2 hours and the resulting solution was stirred for an additional 4 hours. The reaction mixture was washed sequentially, twice with 6N HCl solution (600 mL), twice with saturated NaHCO$_3$ (250 mL), and finally with saturated NaCl (250 mL). The organic solution was dried over anhydrous Na$_2$SO$_4$ and filtered, and the solvent was removed in vacuo to yield 646 g (97%) of 4-chloro-3-nitrobenzoyl-piperidine as a yellow crystalline solid with m.p. =76—78 ° C. IR: 1633, 1535, and 1440 cm$^{-1}$. $^1$H NMR (500 MHz, CDCl$_3$): δ 7.92 (1H, d, J 1.5 Hz), 7.60 (1H, d, J=8.1 Hz), 7.56 (1H, dd, J=8.1 and 1.5 Hz), 3.70 (2H, br s), 3.35 (2H, br s), 1.70 (4H, br s), and 1.56 ppm (2H, br s).

4—Chloro-3-nitro-benzoylpiperidine (539.2 g, 2.00 mol) was dissolved in 2.93 L ethylene glycol in a 5-L flask with stirring and heating to 50 ° C. To this solution, sodium azide (137.0 g, 2.10 moles) was added in portions over 40 min. When the addition was complete, the temperature was increased to 120 ° C. during 2.5 hr and maintained at this temperature for 3 hr. The solution was allowed to cool to 50 ° C, at which time additional sodium azide (65.3 g, 1.00 moles) was added over 5 min. The temperature was increased to 25 120 ° C. during 2.5 hr and maintained at this temperature for 4.5 hr until gas evolution had ceased. The solution was allowed to cool to room temperature, at which time the mixture was partitioned between water and ethyl acetate (1.5 L each). The aqueous phase was extracted three times with ethyl acetate (300 mL). The combined organic phases were washed with 30 mL water, twice with saturated NaCl (200 mL), and finally dried over anhydrous $Na_2SO_2$. The filtered solution was evaporated to yield 345.5 g of crude 1-(benzofurazan-5-ylcarbonyl)piperidine.

Crude 1-(benzofurazan-5-ylcarbonyl)piperidine (22 g) was dissolved in 200 mL ethyl acetate with stirring. Activated charcoal (11.0 g) was added to the solution and the resulting suspension was heated to reflux, allowed to cool to 60° C., and finally filtered with the aid of Celite®. The filtered charcoal was re-suspended in 200 mL ethyl acetate, heated to reflux and again filtered with the aid of Celite®. The filter cake was washed twice with ethyl acetate (50 mL) and the filtrate was concentrated on a rotary evaporator to yield 19.0 g orange oil, which solidified upon standing. The decolorized product was washed with 20 mL ice-cold ethanol to yield 13.1 g pale yellow crystals (2) with m.p. =91.0–93.0° C.

EXAMPLE 3

1-(Benzofurazan-5-ylcarbonyl)piperidine

Benzofurazan-5-carboxylic acid (1 g, 5.6 mmol) was suspended with stirring in 15 mL dichloromethane to which was added carbonyl diimidazole (0.90 g, 5.6 mmol). Gas evolved and the resulting solution was stirred for 40 minutes at which time piperidine (0.5 g, 5.9 mmol) was added with stirring. The reaction solution was concentrated onto silica and product was eluted with hexanelethyl acetate (3:1). Recrystallization from 2-propanol/hexane (1:10) yielded 1-(benzofurazan-5-ylcarbonyl)piperidine (0.94 g, 69%) as a yellow solid with, m.p. 94.5–96.5° C. IR: 2938, 2855, 1620, 1612, 1528, 1487, 1435, 1257, 1233, 1018, 1000, 852, 811, and 747 $cm^{-1}$. $^1H$ NMR (500 MHz): δ 7.10–7.80 (3H, br s); 3.72 (2H br s); 3.39 (2H, br s); 1.72 (4H, br s); and 1.54 ppm (2H, br s).

EXAMPLE 4

Preparation of 4-Fluoropiperidine and 12,3,6-Tetrahydropyridine

N-Trifluoroacetyl-4-hydroxypiperidine (7.92 g, 40 mmol) was suspended in 10 mL dicloromethane and cooled to –78° C. Diethylaminosulfurtrifluoride (6.8 g, 42 mmol) was added and the suspension was allowed to warm to room temperature overnight. The reaction mixture was then diluted with 125 mL dicloromethane and washed with saturated sodium bicarbonate solution, which resulted in vigorous bubbling. The dicloromethane solution was then dried by washing with a saturated sodium chloride solution followed by treatment with anhydrous magnesium sulfate. The solvent was removed in vacuo and the resulting orange oil was stirred with a 7.5 M KOH solution for 1 h at room temperature. The product was extracted into ether and dried with anhydrous magnesium sulfate. The solution was filtered and the ether was removed by atmospheric distillation. The amines were distilled at 95° C. to yield 0.7g colorless oil, which consisted of a mixture of 4-fluoropiperidine/1,2,3,6-tetrahydropyridine. IR: 3317, 3293, 2968, 2955, 2943, 2929, 1451, 1427, 1418, 1377, 1279, and 1023 $cm^{-1}$.

EXAMPLE 5

1-(Benzofurazan-5-ylcarbonyl)-1,2,3,6-tetrahydropyridine (3) and 1-(Benzofurazan-5-ylcarbonyl)4-fluoropiperidine (4)

Benzofurazan-5-carboxylic acid (0.75 g, 4.6 mmol) was suspended in 15 mL dichloromethane. Carbonyl diimidazole (0.75 g, 4.6 mmol) was added to this suspension, which caused the reaction mixture to turned yellow as gas evolved. The solution was stirred for 30 minutes, at which time a mixture of 4-fluoropiperidine and 1,2,3,6-tetrahydropyridine (0.7 g, approximately 7 mmol), prepared as described in Example 4, was added. The solution was stirred for 2 hours at room temperature, at which time the reaction mixture was concentrated onto silica and products were eluted with hexane/ethyl acetate (3:1). Three components were isolated in 100 mg, 200 mg and 300 mg yields. The second eluted compound solidified upon standing and was identified as 1-(benzofurazan-5-ylcarbonyl)-1,2,3,6-tetrahydropyridine, 3 by NMk. M.p. 68.5–70° C. IR: 1630, 1516, 1438, 1245, 1009, 881, 816, 741, and 629 $cm^{-1}$. $^1H$ NMR (500 MHz): δ 7.92 (1H, d, J=9.0 Hz), 7.88 (1H, s), 7.47 (1H, d, J=9.0 Hz); 5.57–5.95 (2H, m); 4.23 (1H, br s); 3.90–3.97 (2H, m); 3.53 (1H, br s); 2.33 (1H, br s); and 2.22 ppm (1H, br s).

The third eluted component was recrystallized from ethyl acetate/hexane (1:10) to yield 200 mg white crystals with m.p. 124–125.5° C. and was identified as 1-(benzofurazan-5-ylcarbonyl)4'-fluoropiperidine, 4 by NMR. IR: 1633, 1439, 1274, 1231, 1034, 923, 881, and 742 $cm^{-1}$. $^1H$ NMR (500 MHz): δ 7.93 (1H, d, J 9.0 Hz); 7.87 (1H, s); 7.44 (1H, d, J=9.0 Hz); 4.9–5.1 (1H, m); 4.0–4.2 (1H, br s); 3.5–3.7 (2H, m); 3.4–3.5 (1H, br s); 1.7–2.1 ppm (4H,m).

EXAMPLE 6

1-(Benzofurazan-5-ylcarbonyl)-1.2.3 .6-tetrahydropyridine (3)

Alternative Method

A more direct route of synthesis of 1-(benzofurazan-5-ylcarbonyl)-1,2,3,$^6$-tetrahydropyridine (3) was also performed in a manner similar to Example 2, Method A, above, starting with pure tetrahydropyridine. Crude product (94% yield) was purified by silica gel chromatography (hexane/ethyl acetate; 1:3), which produced a 74% yield of pale yellow crystals with m.p. 82–83.5° C.; presumably a different crystal isomorph from that obtained above.

EXAMPLE 7

Preparation of 4,4-Difluoropiperidine/1,2,3,6-Tetrahydro-4-fluoropiperidine

N-Trifluoroacetyl-4-piperidone (10 g, 52 mmol) was suspended in 10 mL dicloromethane. To this suspension, diethylaminosulfurtrifluoride (9.1 g, 56.5 mmol) was added. The reaction proceeded slowly at first but brought the mixture to a rolling boil within a few minutes. Cooling was applied to moderate the reaction. The mixture was stirred overnight, diluted with 125 mL dicloromethane and washed with saturated sodium bicarbonate solution, upon which vigorous bubbling was observed. The dicloromethane was then dried with a saturated sodium chloride solution followed by anhydrous magnesium sulfate. The solvent was removed in vacuo and the resulting orange oil was stirred with a 7.5 M KOH solution for 1 h at room temperature. The product was extracted into ether, and the solution was dried with anhydrous magnesium sulfate and filtered. The ether was removed by atmospheric distillation, and the product was distilled at 105–125° C. to yield 4.5 g pale yellow oil, consisting of a mixture of 4,4-difluoropiperidine/1,2,3,6-tetrahydro-4-fluoro-15 piperidine. IR: 2960, 1357, 1265, 1146, 1117,987,952,814, and 792cm$^{-1}$.

EXAMPLE 8

1-(Benzofurazan-5-ylcarbonyl)-4,4-difluoropiperidine (5) and 1-(Benzofurazan-5-ylcarbonyl)-1,2,3,6-tetrahydro4-fluoropyridine (6)

Benzofurazan-5marboxylic acid (0.75 g, 4.6 mmol) was activated in 15 mL dichloromethane with carbonyl diimidazole as above in Example 4. A mixture of 4,4-difluoropiperidine and 1,2,3,6-tetrahydro4-fluoropyridine (0.7 g), prepared as described in Example 7, was added to the solution, which was stirred for 2 hours. The reaction mixture was concentrated onto silica and product was eluted with hexane/ethyl acetate (3:1) yielding two components. The first eluted component was recrystallized from ethyl acetate/hexane (1:5) yielding 480 mg of solid with m.p. 148–149° C. and was identified as 1-(benzofurazami-5-ylcarbonyl)4,4'-difluoropiperidine, 5. IR: 1642, 1440, 1365, 1266, 1123, 1086, 936, 822, 817, 737, 607 cm$^{-1}$. $^1$H NMR (500 MHz): δ 7.96 (1H, d, J=9.5 Hz); 7.90 (1H, s); 7.45 (1H, t, J=8.8 and 1.1 Hz); 3.8–4.1 (2H, br s); 3.5–3.7 (2H, br s); and 1.9–2.2 ppm (4H, br d).

The second eluted component was recrystallized from ethyl acetate/hexane (1:10) yielding 180 mg solid with m.p. 102–105° C. and was identified as 1-(benzofurazan-5-ylcarbonyl)-1,2,3,6-tetrahydro4-fluoropyridine, 6. IR: 1639, 1436, 1361, 1241, 1146, 1007, 828, 817, 742, 605 cm$^{-1}$. $^1$H NMR (500 MHz): δ 7.94 (1H, d, J=9.0 Hz); 7.90 (1H, s); 7.46 (1H, d, J=9.0 Hz); 5.1–5.4 (1H, m); 4.3 (I H, br s); 4.0 (2H, br s); 3.65 (1H, br s); and 2.30–2.55 ppm (2H, br d).

EXAMPLE 9

4-(Benzofurazan-5-ylcarbonyl)morpholine (7)

4-(Benzofurazan-5-ylcarbonyl)morpholine was prepared as described above in Example 2 (Method A), using morpholine in place of piperidine. The product was obtained in 65% yield as a pale crystalline solid with m.p. =148–150 ° C. IR: 1638, 1522, 1439, 1276, 1108, 1003, and 614 cm$^{-1}$. $^1$H NMR (500 MHz): δ 7.94 (1H, d, J=9.2 Hz), 7.88 (1H, s), 7.45 (1H, d, J=9.2 Hz), and 3.50–3.90 ppm (8H, m).

EXAMPLE 10

1-(Benzofurazan-5-ylcarbonyl)-4-cyanopiperidine (8)

Method A 1-(Benzofurazan-5-ylcarbonyl)-4-carboxamidopiperidine was prepared as above in Example 2 (Method A), using 4-cyanopiperidine in place of piperidine. The product was obtained in 74% yield with m.p. =190–192 ° C. following purification by silica gel chromatography with ethyl acetate/methanol (95:5). IR: 1675, 1611, 1431, 1261, and 1226 cm$^{-1}$. $^1$H NMR (200 MHz): δ 7.93 (1H, d, J=9.2 Hz), 7.88 (1H, s), 7.46 (1H, d,J=9.1 Hz), 5.30–5.50 (2H, m), 4.604.70 (1H, m), 3.75–3.85 (1H, m), 2.90–3.25 (2H, m), 2.40–2.50 (1H m), and 1.60–2.10 ppm (4H, m).

Method B 1-(Benzofurazan-5-ylcarbonyl)4-carboxamidopiperidine (2.50 g, 9.11 mmol) was dissolved in CHCl$_3$ (90 mL) and treated with thionyl chloride (1.65 g, 13.8 mmol). The reaction mixture was heated to reflux for 30 minutes, at which time the solution appeared turbid. Additional thionyl chloride (1.52 g, 12.8 mmol) was added and the reaction mixture was heated for an additional 1.5 hr. After the solution cooled to room temperature, it was diluted with CH$_2$Cl$_2$, washed with saturated NaHCO$_3$, and dried over Na$_2$SO$_4$. The product was concentrated onto silica gel and eluted with hexane/ethyl acetate (1:1). The resulting compound was decolorized with charcoal in ethyl acetate to yield 1-(benzofurazan-5-ylcarbonyl)4-cyanopiperidine (0.570 g, 24%) (51% based on recovered starting material) as 30 an oil, which crystallized upon standing as a pale solid with m.p. =104–107° C. IR: 2240, 1735, 1633, 1435, 1271, and 1236 cm$^{-1}$. $^1$H NMR (500 MHz): δ 7.96 (1H, dd, J=9.0 and 1.2 Hz), 7.88 (1H, dd, 1.7 and 0.7 Hz), 7.44 (1H, dd, J=9.1 and 1.6 Hz), 3.60–4.0 (4H, m), 2.95– 3.05 (1H, m), and 1.80–2.15 ppm (4H, m).

EXAMPLE 11

1-(Benzofurazan-5-ylcarbonyl)-4-hydroxypiperidine (9)

1-(Benzofurazan-5-ylcarbonyl)4-hydroxypiperidine was prepared as described above in Example 2 (Method A), using 4-hydroxypiperidine in place of piperidine. The product was obtained in 45% yield with m.p. =132–136 ° C. following purification by silica gel chromatography with ethyl acetate. IR: 1614 and 1446 cm$^{-1}$. $^1$H NMR (200 MHz): δ 7.95 (1H, d, J=9.3 Hz), 7.86 (1H, s), 7.44 (1H, dd, J=9.2 and 1.3 Hz), 4.0–4.25 (2H, m), 3.1–4.0 (3H, m), 1.8–2.1 (2H, m), and 1.5–1.8 ppm (3H, m). $^{13}$C NMR (125 MHz): δ 33.6,34.5, 39.3, 44.6,66.5, 114.6,117.5,130.6, 139.1,148.5, 148.6, and 167.5 ppm.

EXAMPLE 12

1-(Benzofurazan-5-ylcarbonyl)thiomorpholine (10)

1-(Benzofurazan-5-ylcarbonyl)thiomorpholine was prepared as described above in Example 2 (Method A), using thiomorpholine in place of piperidine. The product was 15 obtained in 58% yield as a pale crystalline solid with m.p. =144–146° C. IR: 2912, 1632, 1557, 1434, 1292, 1231, 1208, 957, 941, 880, 825, 741, and 616 cm$^{-1}$. $^1$HNMR (500 MHz): δ 7.94 (1H, d, J=9.6Hz), 7.86 (1H, s), 7.41 (1H, d, J=9.2 Hz), 4.06 (2H, br s), 3.73 (2H, br s), 2.78 (2H, br s), and 2.62 ppm (2H, br s).

EXAMPLE 13

1-(Benzofurazan-5-ylcarbonyl)pvrrolidine (11)

1-(Benzofurazan-5-ylcarbonyl)pyrrolidine was prepared as described above in Example 2 (Method A), using pyrrolidine in place of piperidine. The product was obtained in 61% yield as a pale crystalline solid with m.p. =97.8–99.3 ° C. IR: 2957, 2878, 1632, 1619,1514,1471,1432, 1194, 1009, 882,822,786,and742cm$^{-1}$. $^1$HNMR(500MHz):δ 7.96 (1H, s), 7.91 (1H, d, J=9.0 Hz), 7.58 (1H, d, J=9.5 Hz), 3.69 (2H, t, J=6.6 Hz), 3.50 (2H, t, J=6.5 Hz), 2.01 (2H, q, J=6.6 Hz), and 1.96 ppm (2H, t, J=6.5 Hz).

EXAMPLE 14

1-(Benzofurazan-5-ylcarbonvy)-3-pyrroline (12)

1-(Benzofurazan-5-ylcarbonyl)-3-pyrroline was prepared as described above in 30 Example 2 (Method A), using 3-pyrroline in place of piperidine. The product was obtained in 65% yield as a pale crystalline solid with m.p. =117–118 ° C. IR: 3072,2862,1633,11609, 1562, 1535, 1512,1471, 1460, 1432, 1408, 1360, 1304,1192, 1156, 1012,882,834, 822, 769, 744, 695, 684 cm$^{-1}$. $^1$H NMR (500 MHz): δ 8.00 (1H, s), 7.93 (11H, d, J=9.7 Hz), 7.58 (1H, d, J=9.3 Hz), 5.97 (1H, m), 5.80 (1H, m), 4.50 (2H, s), and 4.30 ppm (2H, s).

EXAMPLE 15

1-(Benzofurazan-5-ylcarbonyl)-4-methylpiperidine (13)

1-(Benzofurazan-5-ylcarbonyl)4-methylpiperidine was prepared as described above in Example 2 (Method A), using 4-methylpiperidine in place of piperidine. The product was obtained in 67% yield with m.p. =86–87 ° C. IR: 1633, 1441, and 1239 cm$^{-1}$. $^1$H NMR (500 MHz): δ 7.92 (1H, d, J=9.5 Hz), 7.90 (1H, s), 7.44 (1H, d, J=9.0 Hz), 4.50–4.70 (1H, m), 3.65–3.80 (1H, m), 3.05–3.15 (1H, m), 2.80–2.90 (1H, m), 1.75–1.85 (1H, m), 1.60–1.75 (2H, m), 1.20–1.30 (1H, m), 1.05–1.20 (1H, m), and 1.00 ppm (3H, d, J=6 Hz).

EXAMPLE 16

1-Benzofurazan-5-ylcarbonyl)hexamethyleneimine (14)

1-(Benzofurazan-5-ylcarbonyl)hexamethyleneimine was prepared as described above in Example 2 (Method A), using hexamethyleneimine in place of piperidine. The product 15 was obtained in 67% yield with m.p. =86–87 ° C. following purification by silica gel chromatography with hexane/ethyl acetate (1:1). IR: 1631, 1428, 1273, and 743 cm$^{-1}$. $^1$H NMR (500 MHz): δ 7.91 (1H, dd, J=8.6, 0.6 Hz), 7.82 (1H, s), 7.44 (1H, dd, J=9.2, 0.8 Hz), 3.72 (2H, t, J=3.9 Hz), 3.43 (2H, t, J=3.9 Hz), 1.88 (2H, t, J=3.9 Hz), and 1.60–1.70 ppm (6H, m).

EXAMPLE 17

1-(Benzofurazan-5-ylcarbonyl)-1,4-dioxa-8-azaspiro [4,5]decane (15)

1-(Benzofurazan-5-ylcarbonyl)-1,4-dioxa-8-azapiro[4,5] decane) was prepared as described above in Example 2 (Method A), using 1,4dioxa-8-azaspiro[4,5]decane (the ethylene ketal of 4-pyridone) in place of piperidine. The product was obtained in 54% yield with m.p.=88–90 ° C. IR: 1638,1440,1268,1120, 1081, and 742 cm$^{-1}$. $^1$HNMR (500 MHz): δ 7.91 (1H, dd, J=9.0, 1.0 Hz), 7.87 (1H, dd, J=1.6, 0.9 Hz), 7.45 (1H, dd, J=9.2, 1.2 Hz)., 4.00 (4H, s), 3.80–3.95 (2H, br s), 2.45–2.65 (2H, br s), 1.75–1.90 (2H, br s), and 1.65–1.75 ppm (2H, br s).

EXAMPLE 18

1-(Benzofurazan-5-ylcarbonyl)-4-piperidone (16)

1-(Benzofurazan-5-ylcarbonyl)4piperidone) was prepared as described above in Example 2 (Method A), using 4-piperidone in place of piperidine. The product was obtained in 30% yield with m.p. =136–139° C. IR: 1715, 1637,1433,1270, and 1238 cm$^{-1}$. $^1$H NMR (500 MHz): δ 7.96 (1H, dd, J=9.6, 1.0 Hz), 7.94 (1H, s), 7.49 (1H, d, J=9.6 Hz), 3.70–4.20 (4H, s), and 2.30–2.80 ppm (4H, br s).

EXAMPLE 19

1-(Benzofurazan-5-ylcarbonyl)4-methoxypiperidine (17)

1-(Benzofurazan-5-ylcarbonyl)-4-hydroxypiperidine (840 mg, 3.40 mmol) was dissolved in dimethylformamide (12 mL) and treated with 60% sodium hydride (150 mg, 3.75 mmol) for 30 minutes. Methyl iodide (650 mg, 4.54 mmol) was added, and, after 3 hours at room temperature, the reaction mixture was further treated with the same quantities of sodium hydride and methyl iodide as above and allowed to stand for 16 hr. The reaction solution was diluted with water and product was extracted into ethyl acetate. The organic solution was washed with water and saturated sodium chloride and dried over MgSO$_4$. The crude product was purified by decolorization with charcoal in ethanol, twice chromatographed on silica gel by elution with hexane/ethyl acetate (2:1), and finally by kugelrohr distillation at 125–140° C. to yield 1-(benzofurazan-5-ylcarbonyl)-4-methoxypiperidine (269 mg, 30%) as a pale yellow oil. IR: 1639, 1440, 1274, 1101, and 1089 cm$^{-1}$. $^1$H NMR (500 MHz): δ 7.91 (1H, dm, J=9.2 Hz), 7.85 (1H, t, J=1.1 Hz), 7.43 (1H, dd, J=9.2 and 1.2 Hz), 3.90–4.05 (1H, m), 3.55–3.72 (2H, m), 3.53 (1H, sept, J=3.5 Hz), 3.38 (3H, s), 3.20–3.35 (1H, m), 1.90–2.02 (1H, m), 1.65–1.85 (2H, m), and −1.65 ppm (1H, m).

EXAMPLE 20

1-(Benzofurazan-5-ylcarbonyl) decadeuteropiNeridine (18)

Benzofurazan-5-carboxylic acid (0.9070 g, 5.526 mmol) was suspended in 15 mL methylene chloride. To this solution, carbonyl diimidazole (0.9027 g, 5.567 mmol) was added. The reaction mixture turned dark as gas evolved. The solution was stirred for 30 minutes, at which time piperidine-d$^{11}$ (0.5125 g, 5.437 mmol) was added. The reaction mixture was stirred for two hours at room temperature, concentrated onto silica gel, and eluted with hexane/ethyl acetate (2:1) to yield 1-(benzofurazan-5-ylcarbonyl)decadeutero-piperidine (911.1 mg, 69%) as a pale crystalline solid with m.p. =88–89 ° C. IR: 2213, 2113, 1624, 1517, 1416, 1233, 1103, 970, 930, 897, 881, 872, 772, 740, and 605 cm$^{-1}$. $^1$H NMR (500 MHz): δ 7.91 (I H, d, J=9.8 Hz), 7.84 (1H, s), and 7.44 ppm (1H, dd, J=9.4 and 1.4 Hz).

EXAMPLE 21

In Vitro Physiological Testing

The physiological effects of invention compounds were tested in vitro with slices of rat hippocampus according to the following procedure. Excitatory responses (field EPSPs) were measured in hippocampal slices, which were maintained in a recording chamber continuously perfused with artificial cerebrospinal fluid (ACSF). During a 15–30 minute interval, the perfusion medium was switched to one containing various concentrations of the test compounds. Responses collected immediately before and at the end of drug perfusion were superimposed in order to calculate the percent increase in EPSP amplitude.

To conduct these tests, the hippocampus was removed from anesthetized, 2 month old Sprague-Dawley rats and in vitro slices (400 micrometers thick) were prepared and maintained in an interface chamber at 35° C. using conventional techniques [see, for example, Dunwiddie and Lynch, *J. Physiol.* 276: 353–367 (1978)]. The chamber was constantly perfused at 0.5 mL/min with ACSF containing (in mM): NaCl 124, KCl 3, KH2PO$_4$ 1.25, MgSO$_4$ 2.5, CaCl$_2$ 3.4, NaHCO$_3$ 26, glucose 10 and L-ascorbate 2. A bipolar nichrome stimulating electrode was positioned in the dendritic layer (stratum radiatum) of the hippocampal subfield CAI close to the border of subfield CA3.

Current pulses (0.1 msec) through the stimulating electrode activate a population of the Schaffer commissural (SC) fibers which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field EPSP) which is recorded by a high impedance recording electrode positioned in the middle of the stratum radiatum of CA1.

For the experiments summarized the table, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude. If the responses were stable for 15–30 minutes (baseline), test compounds were added to the perfusion lines for a period of about 15 minutes. The perfusion was then changed back to regular ACSF.

Paired-pulse stimulation was used since stimulation of the SC fibers, in part, activates interneurons which generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("primed") response for data analysis.

The first data column of Table I shows the estimate of the concentration of each test compound that would be required to increase the amplitude of the field EPSP to a value 10% above the baseline level. Values were estimated by interpolation in most cases, but by extrapolation from determined values for others.

EXAMPLE 22

Behavioral Testing

The second data column in Table 1 shows the Minimum Effective Dose (MED$_s$) for activity in a methamphetamine/rat model for assessing the probable efficacy of neuroleptic drugs for the treatment of schizophrenia (Larson el al., *Brain Res.*, supra). The dose recorded is that which reduced the hyperactivity and/or the stereotypic activity induced by acute administration of 2 mg/kg methamphetamine in Sprague-Dawley rats aged 24 months. Activity was monitored for 90 minutes using two rows of multiple, paired infrared diode-detectors such that the lower row detected locomotion and the upper row detected rearing behavior. Data were collected by and stored in a personal computer for later analysis.

While the invention has been described with reference to specific methods and embodiments, it will be appreciated that various modifications may be made without departing from the invention.

It is claimed:

1. A compound having the structure:

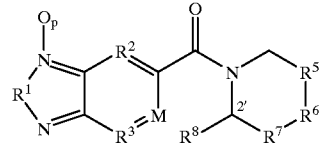

in which:

R$^1$ is oxygen or sulfur;

R$^2$ and R$^3$ are independently selected from the group consisting of —CR═and —CX═;

M is ═CR$^4$—, wherein R$^4$ and R$^8$ are independently R or together form a moiety which links M to the ring vertex 2' to form a ring, the moiety which links being selected from the group consisting of a single bond, —CRR'—, —CR═CR'—, —C(O)—, —O—, —S(O)$_y$—, —NR—, and —N═;

R$^5$ is —(CRR')$_n$—, ;

R$^6$ is —O—; and

R$^7$ is selected from the group consisting of—CRR'—, —C(O)—, —CXX'— and —CRX—;

wherein

X and X' are independently selected from —Br, —Cl, —F, —CN, —NO$_2$, —OR, —SR, —NRR',—C(O)R, —CO$_2$R, or —CONRR', wherein two groups R or R' on an individual group X, or on two adjacent groups X, may together form a ring; and R and R' are independently selected from (i) hydrogen, (ii) C$_1$–C$_6$ branched or unbranched alkyl or C$_3$ to C$_6$ cycloalkyl groups, which may be unsubstituted or substituted with one or more functionalities selected from halogen, nitro, alkoxy, hydroxy, alkylthio, amino, keto, aldehyde, carboxylic acid, carboxylic ester, or carboxylic amide, and wherein when R and R' are alkyl groups, said alkyl groups may together form a ring, and (iii) aryl groups, which may be unsubstituted or substituted with one or more functionalities selected from halogen, nitro, alkoxy, hydroxy, aryloxy, alkylthio, amino, keto, aldehyde, carboxylic acid, carboxylic ester, or carboxylic amide;

p is 0 or 1; and n is one and y is 0, 1 or 2.

2. A compound in accordance with claim 1 in which R and R' are independently selected from (i) hydrogen and (ii) C$_1$–C$_6$ branched or unbranched alkyl or C$_3$ to C$_6$ cylcoalkyl groups, which may be unsubstituted or substituted with one or more functionalities selected from halogen, nitro, alkoxy, hydroxy, alkylthio, amino, keto, aldehyde, carboxylic acid, carboxylic ester, or carboxylic amide, and wherein when R and R' are alkyl groups, said alkyl groups may together form a ring.

3. A compound in accordance with claim 1 in which R$^2$ and R$^3$ are —CR═ and M is ═CR$^4$—.

4. A compound in accordance with claim 3 in which p is 0, R$^1$ is oxygen, and R$^4$ and R$^8$ are hydrogen.

5. A compound in accordance with claim 4 in which $R^5$ and $R^7$ are $-(CRR')_n-$.

6. A compound in accordance with claim 5 in which R and R' are hydrogen, said compound being 4-(benzofurazan-5-ylcarbonyl)morpholine.

7. A compound in accordance with claim 1 wherein $R^4$ and $R^8$ together form a moiety which links M to the ring vertex 2' form a ring, the moiety which links being a single bond, $-CRR'-$, $-CR=CR'-$, $-C(O)-$, $-O-$, $-S-$, $-NR-$, or $-N=$.

8. A compound in accordance with claim 7 in which $R^2$ and $R^3$ are $-CR=$.

9. A pharmaceutical composition comprising an effective amount of the compound according to claim 1 in combination with a pharmaceutically acceptable carrier, additive or excipient.

10. A pharmaceutical composition comprising an effective amount of the compound according to claim 2 in combination with a pharmaceutically acceptable carrier, additive or excipient.

11. A pharmaceutical composition comprising an effective amount of the compound according to claim 3 in combination with a pharmaceutically acceptable carrier, additive or excipient.

12. A pharmaceutical composition comprising an effective amount of the compound according to claim 4 in combination with a pharmaceutically acceptable carrier, additive or excipient.

13. A pharmaceutical composition comprising an effective amount of the compound according to claim 5 in combination with a pharmaceutically acceptable carrier, additive or excipient.

14. A pharmaceutical composition comprising an effective amount of the compound according to claim 7 in combination with a pharmaceutically acceptable carrier, additive or excipient.

15. A pharmaceutical composition comprising an effective amount of the compound according to claim 8 in combination with a pharmaceutically acceptable carrier, additive or excipient.

16. A method of enhancing AMPA receptor function in a mammalian subject in need thereof comprising administering to said subject an effective amount of a compound according to claim 1.

17. The method according to claim 16, wherein said enhancing is effective to alleviate impairment of memory, or other cognitive functions caused by a hypoglutamatergic condition or by deficiency in the number or strength of excitatory synapses or in the number of AMPA receptors.

18. The method according to claim 16, wherein said enhancing is effective to treat schizophrenia, or schizophreniform behavior resulting from a cortical/striatal imbalance caused by a hypoglutamatergic condition or by deficiency in the number or strength of excitatory synapses or in the number of AMPA receptors.

19. The method according to claim 16, wherein said enhancing is effective to facilitate learning of behaviors dependent on AMPA receptor functioning.

20. The method according to claim 16, wherein in said compound R and R' are independently selected from (i) hydro and (ii) $C_1-C_6$ branched or unbranched alkyl groups which may be unsubstituted or substituted with one or more functionalities selected from halogen, nitro, alkoxy, hydroxy, alkylthio, amino keto, aldehyde, carboxylic acid, carboxylic ester, or carboxylic amide, and wherein R and R' are alkyl group, said alkyl groups may together form a ring.

21. The method according to claim 17, wherein said compound is 4-benzofurazan-5-ylcarbonyl)morpholine.

* * * * *